(12) United States Patent
Hansen

(10) Patent No.: US 9,398,848 B2
(45) Date of Patent: Jul. 26, 2016

(54) EYE GAZE TRACKING

(75) Inventor: Dan Witzner Hansen, Olstykke (DK)

(73) Assignee: IT-UNIVERSITY OF COPENHAGEN, Copenhagen S (DK)

( * ) Notice: Subject to any disclaimer, the term of this patent is extended or adjusted under 35 U.S.C. 154(b) by 137 days.

(21) Appl. No.: 13/003,030

(22) PCT Filed: Jul. 8, 2008

(86) PCT No.: PCT/DK2008/000257
§ 371 (c)(1),
(2), (4) Date: Apr. 7, 2011

(87) PCT Pub. No.: WO2010/003410
PCT Pub. Date: Jan. 14, 2010

(65) Prior Publication Data
US 2011/0182472 A1    Jul. 28, 2011

(51) Int. Cl.
| | | |
|---|---|---|
| *G06K 9/00* | (2006.01) |
| *A61B 3/113* | (2006.01) |
| *G02B 27/00* | (2006.01) |
| *G06T 7/00* | (2006.01) |
| *G06F 3/01* | (2006.01) |
| *G06F 3/03* | (2006.01) |
| *H04N 13/04* | (2006.01) |

(52) U.S. Cl.
CPC ............ *A61B 3/113* (2013.01); *G02B 27/0093* (2013.01); *G06F 3/011* (2013.01); *G06F 3/013* (2013.01); *G06F 3/0325* (2013.01); *G06K 9/00604* (2013.01); *G06T 7/004* (2013.01); *H04N 13/0484* (2013.01)

(58) Field of Classification Search
USPC .......... 382/100, 103, 117, 190, 291; 351/209, 351/210; 345/156, 157
See application file for complete search history.

(56) References Cited

U.S. PATENT DOCUMENTS

| 4,836,670 A | 6/1989 | Hutchinson |
| 5,016,282 A * | 5/1991 | Tomono et al. ............... 382/117 |

(Continued)

OTHER PUBLICATIONS

Guestrin, E.D.; Eizenman, M., General Theory of Remote Gaze Estimation Using the Pupil Center and Corneal Reflections, Jun. 2006; 1124-33; vol. 53, Jun. 5, 2006.

*Primary Examiner* — Eric Rush
(74) *Attorney, Agent, or Firm* — Day Pitney LLP

(57) ABSTRACT

A method of performing eye gaze tracking of at least one eye of a user, by determining the position of the center of the eye, said method comprising the steps of:
  detecting the position of at least three reflections on said eye,
  transforming said positions to spanning a normalized coordinate system spanning a frame of reference,
  detecting the position of said center of the eye relative to the position of said reflections and transforming this position to said normalized coordinate system,
  tracking the eye gaze by tracking the movement of said eye in said normalized coordinate system.
Thereby calibration of a camera, such as knowledge of the exact position and zoom level of the camera, is avoided. Further, it is not necessary to know the position of light sources. This results in a much more flexible and user friendly system.

10 Claims, 4 Drawing Sheets

(56) References Cited

U.S. PATENT DOCUMENTS

| | | | |
|---|---|---|---|
| 5,231,674 A * | 7/1993 | Cleveland et al. | 382/117 |
| 5,481,622 A * | 1/1996 | Gerhardt et al. | 382/103 |
| 5,668,622 A | 9/1997 | Charbounier et al. | |
| 5,912,721 A * | 6/1999 | Yamaguchi et al. | 351/210 |
| 6,152,563 A * | 11/2000 | Hutchinson et al. | 351/209 |
| 6,553,281 B1 * | 4/2003 | Liu | 700/302 |
| 6,659,611 B2 * | 12/2003 | Amir et al. | 351/210 |
| 7,963,652 B2 * | 6/2011 | Vertegaal | G06K 9/00604 351/205 |
| 2004/0196214 A1 * | 10/2004 | Maguire, Jr. | 345/8 |
| 2005/0175218 A1 * | 8/2005 | Vertegaal et al. | 382/103 |
| 2006/0013505 A1 * | 1/2006 | Yau et al. | 382/285 |
| 2006/0050087 A1 * | 3/2006 | Tanimura | G06F 3/011 345/629 |
| 2006/0110008 A1 | 5/2006 | Vertegaal et al. | |

\* cited by examiner

EYE GAZE TRACKING

FIELD OF THE INVENTION

As one of the most salient features of the human face, eyes play an important role in interpreting and understanding a person's desires, needs, cognitive processes, and emotional states. The importance of eye gaze is implicitly acknowledged as it is used for inspection of our surroundings and is important in social interaction. Robust nonintrusive eye detection and tracking is therefore crucial for human computer interaction, attentive user interfaces and understanding human affective states.

Eye gaze estimation and tracking are important for many applications including human attention analysis, human cognitive state analysis, gaze-based interactive user interfaces, gaze contingent graphical display, and human factors. An eye gaze tracker is a device for analyzing eye gaze movements. As the eye scans the environment or fixates on particular objects in the scene, an eye gaze tracker simultaneously localizes the eye position in the image and tracks its movement over time to determine the direction of gaze.

A method of tracking eye gaze is based on corneal reflection. Corneal reflection eye gaze tracking systems project light toward the eye and monitor the angular difference between pupil position and the reflection of the light beam from the cornea surface. Near-infrared light is often employed, as users cannot see this light and are therefore not distracted by it. The light reflected from the eye has two major components. The first component is a 'glint', which is a very small and very bright virtual image of the light source reflected from the front surface of the corneal bulge of the eye; the glint is also known as the first Purkinje image. The second component is light that has entered the eye and has been reflected back out from the retina. This light serves to illuminate the pupil of the eye from behind, causing the pupil to appear as a bright disk against a darker background. This retro-reflection, or "bright eye" effect familiar to flash photographers, provides a very high contrast image. An eye gaze tracking system determines the center of the pupil and the glint and the change in the distance and direction between the two as the eye is rotated. The orientation of the eyeball can be inferred from the differential motion of the pupil center relative to the glint.

The main components of a typical corneal reflection eye gaze tracking system include a video camera sensitive to near-infrared light, a near-infrared light source (often a light-emitting diode), typically mounted to shine along the optical axis of the camera, and a computer system for analyzing images captured by the camera. The on-axis light source is positioned at or near the focal center of the camera. Image processing techniques such as intensity threshold and edge detection identify the glint and the pupil from the image captured by the camera using on-axis light, and locates the pupil center in the camera's field of view.

Known systems typically require a lot of cumbersome calibration both in relation to the positioning of the camera and the light sources, and therefore a system for eye gaze tracking without calibrated cameras, direct measurements of specific users' eye geometries or requiring the user to visually track a cursor traversing a known trajectory is needed.

U.S. Pat. No. 6,659,611 describes a system and method for eye gaze tracking without calibrated cameras, direct measurements of specific users' eye geometries or requiring the user to visually track a cursor traversing a known trajectory.

The preferred embodiment includes two uncalibrated cameras imaging the user's eye and having on-axis lighting. The cameras capture images of a test pattern in real space as reflected from the user's cornea, which is essentially a convex spherical mirror. The invention then extracts parameters required to define a mathematical mapping between real space and image space, including spherical and perspective transformations. The invention processes subsequent images of objects reflected from the user's eye through the inverse of the mathematical mapping to determine a gaze vector and a point of regard. Alternatively, a single calibrated camera may be employed with means for estimating the eye-to-camera distance. A head-mounted embodiment that may include a laser pointer is also described. Problems with this solution are that when using one camera, calibration comprising determining the distance between eye and camera is required, but since this distance might change during use, it will result in errors in the eye gaze tracking. In order to avoid this limitation and calibration process, two cameras are required. Further, when using this method it is necessary to know the exact position of the light sources, which makes the solution quite inflexible.

OBJECT AND SUMMARY OF THE INVENTION

The object of the invention is to find a simple and easy eye gaze tracking method, which solves or at least reduces the above drawbacks.

This is obtained by a method of performing eye gaze tracking of at least one eye of a user, by determining the position of the central eye, said method comprising the steps of:
  detecting the position of at least three reflections on said eye,
  transforming said positions to spanning a normalized coordinate system spanning a frame of reference,
  detecting the position of said central eye relative to the position of said reflections and transforming this position to said normalized coordinate system,
  tracking the eye gaze by tracking the movement of said eye in said normalized coordinate system.

Thereby calibration of the camera, such as knowledge of the exact position and zoom level of the camera, is avoided. Further, it is not necessary to know the position of light sources. This results in a much more flexible and user friendly system being easier to set up and less expensive than known systems.

Further, the method is robust to head position, since the user does not have to stay in a fixed position Further, the lights and camera can be positioned in any position, making the method very flexible.

Further, the exact position of lights and camera needs not be known. The initial calibration of looking at a predefined set of points needs not be repeated if the system set-up has been changed accidentally provided the geometry is not changed.

Further, the method can be used with all kinds of light sources (focal, linear circular) and also light from the screen can be used as light source (i.e. no external light sources needed). This results in a less expensive system.

Further, since no calibration of the camera is needed, the method is more flexible and the user can change the zoom of the camera without affecting the result.

In a specific embodiment said reflections are obtained by projecting light sources towards said at least one eye of said user.

In a specific embodiment the step of transforming said positions to spanning a normalized coordinate system is performed using a bilinear transformation function.

In a specific embodiment the eye gaze is tracked to determine towards which points on a surface said user is gazing.

In a specific embodiment said surface is a screen surface on a monitor.

In a specific embodiment mapping between the eye gazing and said surface coordinates is obtained via a calibration process where the user is requested to look at a number of predefined points on said surface.

The invention further relates to a computer-readable medium having stored therein instructions for causing a processing unit to execute a method according to the above.

The invention further relates to a system for performing eye gaze tracking of at least one eye of a user by determining the position of the central eye, said method comprising the steps of:
- means for detecting the position of at least three reflections on said eye,
- means for transforming said positions to spanning a normalized coordinate system spanning a frame of reference,
- means for detecting the position of said central eye relative to the position of said reflections and transforming this position to said normalized coordinate system,
- means for tracking the eye gaze by tracking the movement of said eye in said normalized coordinate system.

BRIEF DESCRIPTION OF THE DRAWINGS

In the following, preferred embodiments of the invention will be described referring to the figures, where.

DESCRIPTION OF EMBODIMENTS

In FIG. 1 the principle behind eye gaze tracking according to the present invention is illustrated. In FIG. 1A is illustrated an eye 100 with the cornea 101 covering the central pupil 102 and the iris 104 and as seen or monitored by a camera, another person or another image detection system (not shown).

Figure 1A:
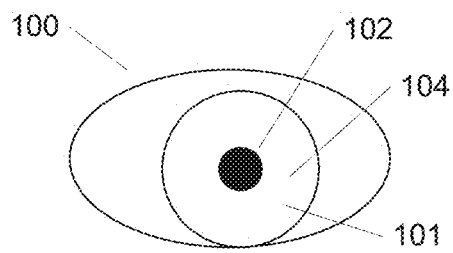
FIG. 1 illustrates the principle behind eye gaze tracking according to the present invention.
Figure 1B:
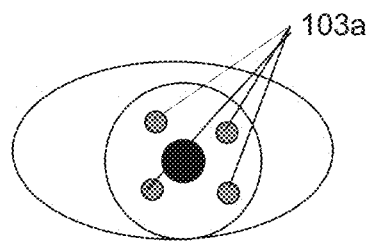

The method of eye tracking presented in the following is based on the corneal reflections 103a of a number of light sources as sketched in FIG. 1B. According to the present method, light from four different sources is projected toward the eye, and the reflections or glints 103 are detected and measured.

In this example 4 light sources are used, but in another embodiment three light sources could be used. This would though require a special normalization procedure. Normalization of data according to 3 light sources can be done when (for example) using one of the light sources as the origin and then using the ratios of the lines from the origin to the other two reflections. The normalization mapping may thus be a homology Further, even more than 4 light sources could be used thereby increasing the robustness and avoiding errors if one light source should fail or be obscured. This ensures that there are always 4 reflections in the eye.

As mentioned in the introduction, near-infrared light is often employed, as users cannot see this light and are therefore not distracted by it. However, other types of light may also be used (just as long as 3-4 stable reflections can be monitored). The four light sources may be placed arbitrarily.

In other words, no information on the exact position, direction, condition etc. of the light sources is needed, which is a huge advantage compared to conventional eye tracking methods. Apart from the positions of the glints 103, also the ellipses of the pupil 102 and/or the iris 104 can be detected and measured. These parameters can be extracted by different methods such as for instance by a feature-based method, or by a so-called appearance-based method where the pixel values are used. In appearance-based methods the eye features are not extracted explicitly, but the image pixels are used directly as input for the gaze mapping function.

Measurements from at least one eye are necessary to determine eye gazing, and if the person moves his head swiftly, then the other eye can be used. Based on the shape of the eye, it is possible to detect whether the measurements are based on the right or left eye and correspondingly adapt the eye gazing calculations. When eye gazing is based on both eyes, it will lead to more robust eye gaze measurements.

Further, if the camera has been pre-calibrated, it is possible to use the method for determining several Euclidian measurements, such as the 3D gaze direction vector or the angular position of the pupil relative to the camera by measuring e.g. a 3d vector between the eye and the screen.

Figure 1C:
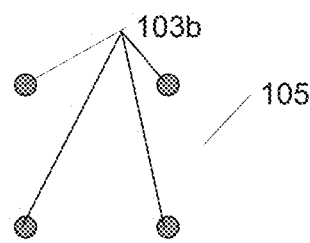

The four reflections or glints 103 from one cornea 102 are then used to normalize the data as illustrated in FIG. 1C, where the four reflections 103b are shown in the normalized reflection space 105. The normalization is performed using a bilinear transformation function (a Möbius transformation) H, and the reflections in the image are then transformed into four new coordinates. These could for instance be {(0,0), (1,0), (0,1) and (1,1)} or they could relate to the positions of the light sources—e.g. {(0,0), (screen width, 0), (0, screen height), (screen width, screen height)} in the case of the light sources being placed in the corners of a rectangular screen. The normalized reflection space 105 then constitutes a frame of reference for all other data. Hereby the method is feature-based, and the reflections in the cornea in the normalized reflection space are projectively invariant and hence independent of the position of the head as such. The reference feature could be either the pupil, the center of or the entire iris ellipse or a region of pixels or points or the entire image. In an alternative embodiment, when performing the normalization, either the iris or the pupil could be mapped to a circle, and then afterwards a similar mapping is used to map the four reflections.

A non-linear normalization function could also be employed instead of the linear—thereby enabling for instance taking the curvature of the screen surface into account. Non-linear correction of the normalisation points (glints) moves the points in a non-linear fashion. The purpose of non-linear correction of the normalisation points (glints) could be to account for non-linearities in the observed glint positions and differences between the true pupil position (in 3D space) and the plane defined by the glints.

This may be done directly from the image space coordinates or alternatively after performing a linear normalisation. For example, a direct mapping from the image space map each observed glint position according to a second order polynomial.

The non-linear correction after the normalisation could be performed by moving each glint position along straight lines. Alternatively it could also be performed differently for each glint.

Figure 1D:
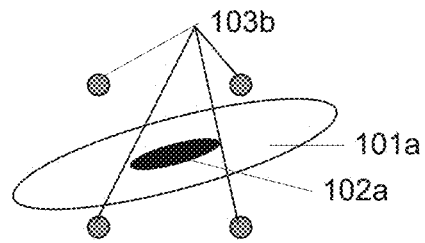

In FIG. 1D is sketched the ellipses of the eye cornea 101a and eye pupil 102a in the normalized reference space 105.

Figure 1E:
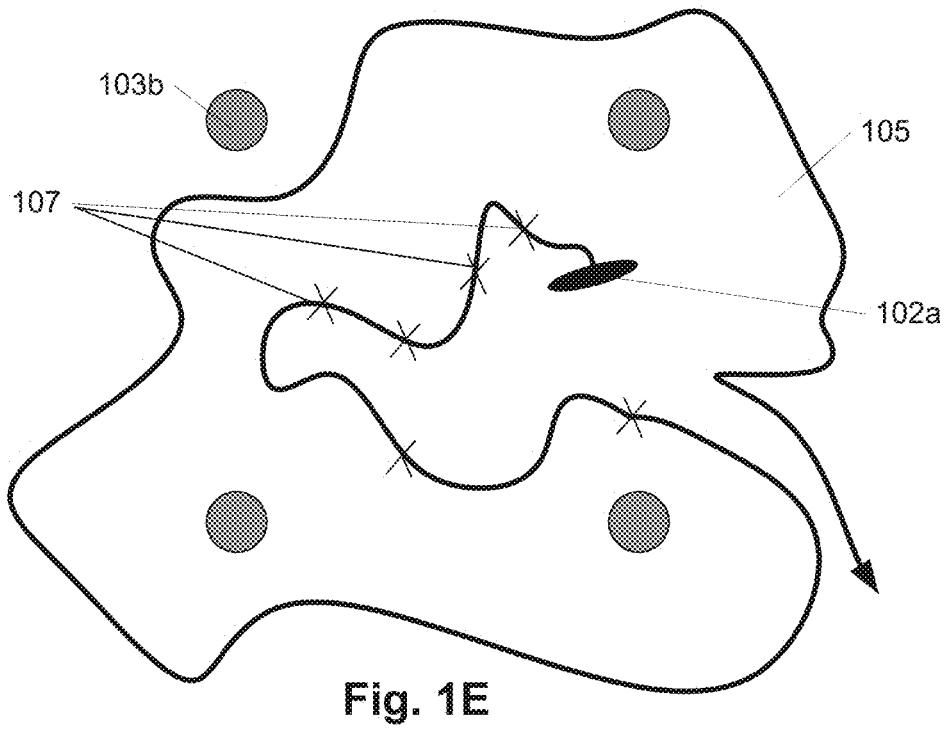

The eye tracking is then illustrated in FIG. 1E depicting the monitored positions 107 (connected by a line) of the center of the eye pupil 102a in the normalized reflection space over a period of time.

Figure 2:
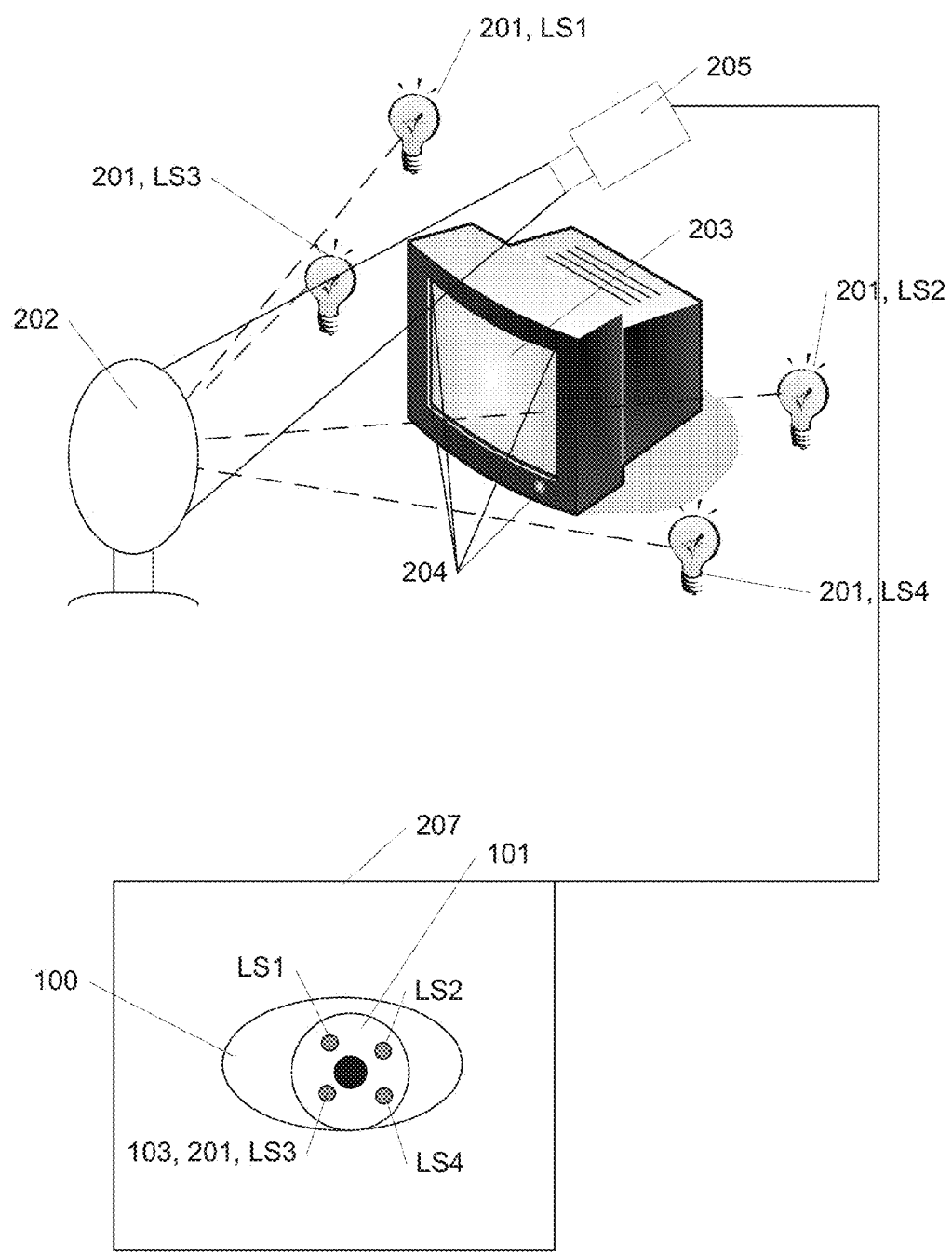
FIG. 2 illustrates a system for determining eye gaze according to the present invention.

FIG. 2 illustrates a system for determining the eye gaze of a user 202 according to the present invention. In the embodiment the system comprises a total of four light sources 201 (LS1-LS4) which can be placed arbitrarily as long as some of the light from all four sources hits at least one eye of the user 202 of the system. In the contrary to other eye tracking methods according to prior art, the positions and nature (intensity, light direction etc) of the light sources 201 need not be known and can hence be placed from session to session wherever most convenient for the user 202. As the method is effective with all kinds of light sources (focal, linear, circular), also light from a screen 203 can be used as light sources whereby it is achieved that no external light sources are in fact needed. Thus, it is also possible to use the four reflections of the screen corners 204 in an eye cornea of the user 202 as an alternative to the four light sources 201.

One or more image capturing devices 205, such as a camera or a video camera, is placed with a free view to the (at least) one eye 100 of the user 202. In alternative embodiments other devices could be used for detecting respectively the eye reflections and relevant eye characteristics. The image capturing device 205 then takes a picture or image 207 or in another way monitors the eye with the reflections 103 of the four light sources 201. One single image capturing device is enough for the system to perform the eye tracking, but the use of one or more further cameras could make the method more robust in that the data amount is then similarly increased making the extracted positions and vectors more accurate and reliable. Also the use of two cameras would increase the field of view within which the user needs to keep his or her eye. The system could also be mounted so that the first image capturing device monitors one user and the second image capturing device monitors another user—thereby better taking e.g. squinting or other uncertainty raising effects into account. Like the case with the light sources, the exact position of the image capturing device(s) needs not be known.

Finally, the eye tracking system comprises one or more monitors (in fact any planar object will do, e.g. a wall or window) 203 of some sort on which the eye tracking is performed and the gaze of the user can be detected and optionally followed. Again, the exact placing of the screen 203 is not needed in the presented eye tracking method.

In one situation a user could employ the eye tracking method while moving around in e.g. a wheelchair under different environmental conditions (direct sun, shade etc), where the system is simply constituted by a laptop with a single camera.

The light sources being used should be chosen such that the reflections can be generated on the eye. As long as this is the case, any light source can be used. Further, even moving light sources could be used as long as they move coherently (e.g. together with the view-plane (screen) or with known geometry). Hereby this movement can be compensated in the following normalization.

Figure 3:
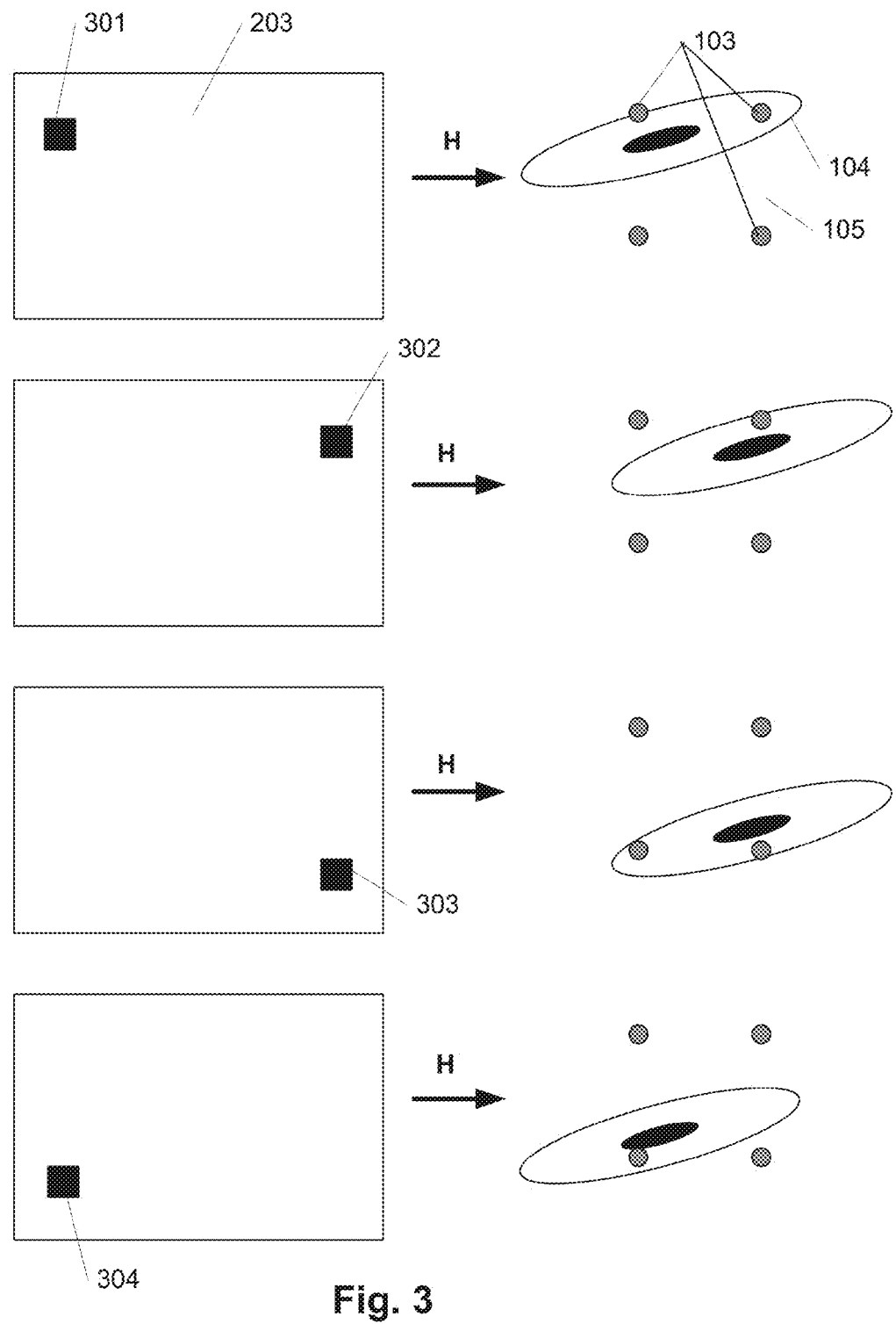
FIG. 3 illustrates a method of calibrating the system according to the present invention.

Prior to performing the eye tracking itself, the system has to be calibrated, which according to the method can be done in a very simple, fast and straight forward way as illustrated in FIG. 3. The calibration could in one embodiment be performed before each session.

The calibration is performed by asking the user to look at at least four different points (301-304)—either on the screen (viewing plane) 203 or outside the screen—as long as the system has knowledge on the positions relative to the screen. For each of these points (301-304) a corresponding image of the light reflections in the cornea is taken. From these data the bilinear transformation function H between the four reflections in each image and the four points in the normalized reflection space 105 (such as $\{(0,0), (1,0), (0,1)$ and $(1,1)\}$ as used above) is determined. The transformation function H is then used to transform any other data from the image to the normalized reflection space 105 such as for instance the ellipsis of the iris 104 or even the entire picture.

From this a function G mapping data from the normalized reflection space 105 into screen coordinates is then determined. If G is linear, then the function G can be described by yet another Möbius transformation (in addition to the initially chosen transformation function H). As the combination of two bilinear functions is itself bilinear, the whole mapping can be described as a bilinear Möbius transformation implicitly performing a normalization. Alternatively, G is a nonlinear function such as e.g. a neural network, a Gaussian process, a spline interpolation etc. Having determined G, the calibration of the system is performed, and the eye movement can be tracked.

After the calibration of the system as described above, and as further image data are collected, the data are normalized via the four monitored reflections in the cornea from the four light sources and thereafter mapped to screen coordinates by the use of the G.

Figure 4:
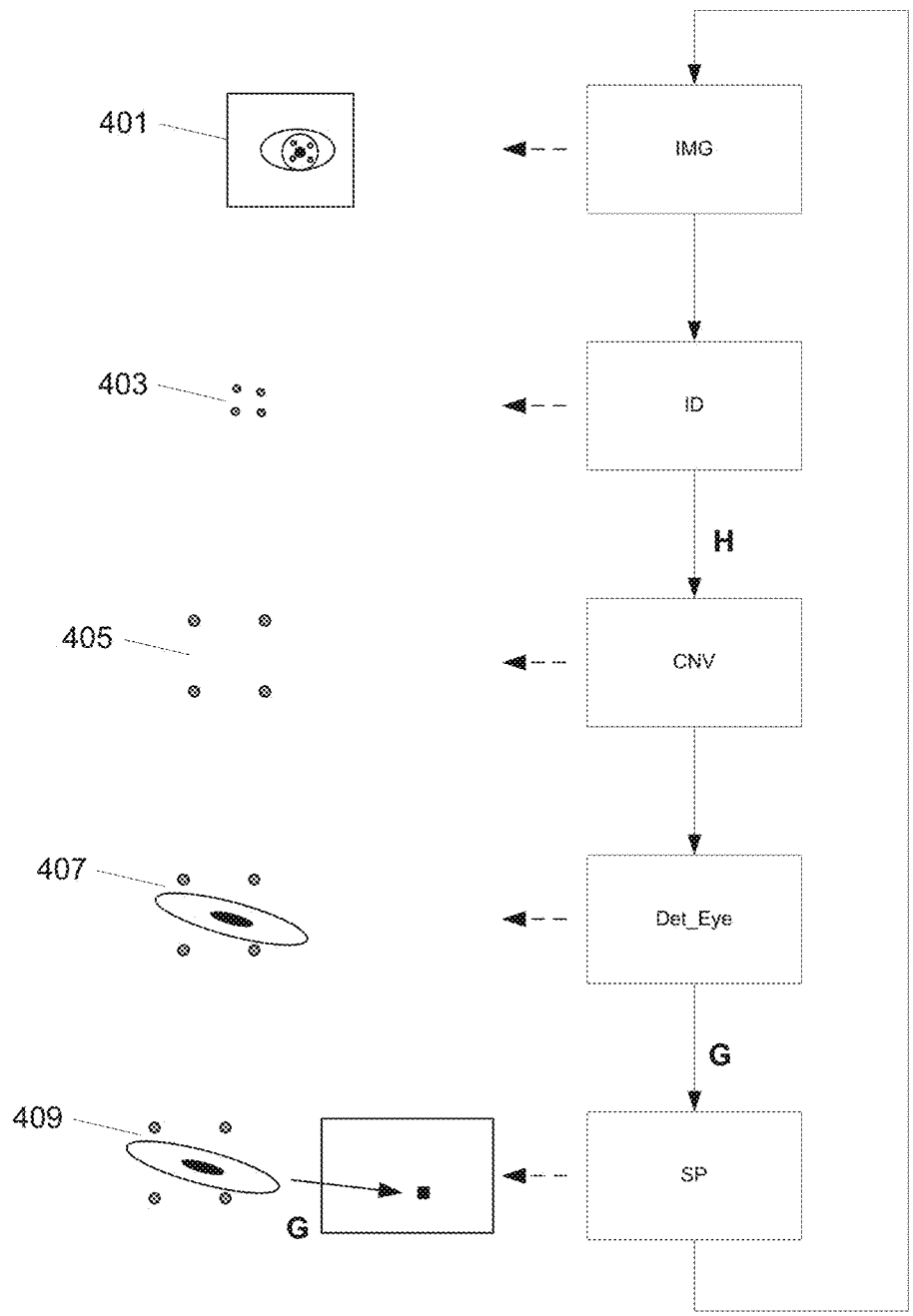
FIG. 4 illustrates a method of determining eye gaze according to the present invention.

FIG. 4 illustrates a method of tracking eye gaze after the calibration has been performed. In the first step (IMG) an image 401 is made of the eye of the user, where the four reflections are visible in the image. In the next step (ID) the four reflections 403 are identified using standard image recognition methods. In the next step (CNV) the four reflections are transformed as described above into a normalized reflection space 405. Next (Det_Eye) reference features of the eye (407) are transformed to the same normalized reflection space. Finally, in the last step (SP) the relative position of the reference features of the eye in the normalized reflection space 409 is determined in order to determine the eye gaze. This process then restarts performing the same steps on a new picture.

Further, the system is a method of determining eye gazing and is not limited to determining eye gazing on a monitor screen, but could actually be used for determining eye gazing towards any surface. Therefore the word screen in the above could actually be substituted by the word surface or eye gazing surface.

The invention claimed is:

1. A method of performing eye gaze tracking of at least one eye of a user, by determining the position of a central eye, the method comprising the steps of:
   in an image of said central eye, detecting, by means of one or more uncalibrated cameras, two-dimensional positions of at least three glint reflections on said central eye,
   normalizing the two-dimensional positions of the at least three glint reflections by a transformation to span a normalized coordinate system spanning a frame of reference, wherein the transformation is estimated only from the positions of the at least three glint reflections on said central eye in the image and at least three randomly-located two-dimensional coordinates in said normalized coordinate system, wherein the transformation is a Möbius transformation, and wherein said normalizing is done without a three-dimensional representation or geometrical encoding of either the positions of the glint reflections or the two-dimensional coordinates;
   detecting the position of said central eye relative to the positions of said glint reflections and, by means of the transformation, transforming this position to said normalized coordinate system, and tracking the eye gaze by tracking the movement of said central eye in said normalized coordinate system.

2. A method according to claim 1, wherein said glint reflections are obtained by projecting light sources towards said at least one eye of said user.

3. A method according to claim 1, wherein the eye gaze is tracked to determine towards which points on a surface said user is gazing.

4. A method according to claim 3, wherein said surface is a screen surface on a monitor.

5. A method according to claim 3, wherein mapping between the eye gazing and surface coordinates of said surface is obtained via a calibration process where the user is requested to look at a number of predefined points on said surface.

6. A method according to claim 5, further comprising transforming the movement of said central eye from said normalized coordinate system to said surface coordinates of said surface on which the user is gazing using a second transformation being a linear transformation or a non-linear transformation, wherein the transformations occur sequentially such that the eye gaze tracking occurs when the transformation is of reference features of the central eye to the normalized coordinate system, and wherein the second transformation is of the eye gaze to the surface coordinates of the surface.

7. A method according to claim 1, wherein the step of transforming said positions to span a normalized coordinate system is performed using a bilinear transformation function.

8. A non-transitory computer readable medium having stored therein instructions for causing a processing unit to execute a method according to claim 1.

9. A system for performing eye gaze tracking of at least one eye of a user by determining the position of a central eye, the system comprising:

means for detecting, by means of one or more uncalibrated cameras, two-dimensional positions of at least three glint reflections on said central eye in an image of said central eye, means for normalizing the two-dimensional positions of the at least three glint reflections by a transformation to span a normalized coordinate system spanning a frame of reference, wherein the transformation is estimated only from the positions of the at least three glint reflections on said central eye in the image and at least three, randomly-located two-dimensional coordinates in the normalized coordinate system, wherein the transformation is a Möbius transformation, and wherein said normalizing is done without a three-dimensional representation or geometrical encoding of either the positions of the glint reflections or the two-dimensional coordinates;

means for detecting the position of said central eye relative to the positions of said glint reflections and, by means of the transformation, transforming this position to said normalized coordinate system, and means for tracking the eye gaze by tracking the movement of said central eye in said normalized coordinate system.

10. A system according to claim 9, further comprising means for transforming the movement of said central eye from said normalized coordinate system to surface coordinates of a surface on which the user is gazing using a second transformation being a linear transformation or a nonlinear transformation, wherein the transformations occur sequentially such that the eye gaze tracking occurs when the transformation is of reference features of the central eye to the normalized coordinate system, and then the second transformation is of the eye gaze to the surface coordinates of the surface.

\* \* \* \* \*